(12) United States Patent
Baroni et al.

(10) Patent No.: US 9,982,264 B2
(45) Date of Patent: May 29, 2018

(54) ANTISENSE COMPOSITIONS AND METHODS OF MAKING AND USING SAME

(71) Applicant: Nogra Pharma Limited, Dublin (IE)

(72) Inventors: Sergio Baroni, Villa D'adda (IT);
Salvatore Bellinvia, Mendrisio (CH);
Francesca Viti, Salorino (CH)

(73) Assignee: Nogra Pharma Limited, Dublin (IE)

( * ) Notice: Subject to any disclaimer, the term of this patent is extended or adjusted under 35 U.S.C. 154(b) by 0 days. days.

(21) Appl. No.: 15/130,737

(22) Filed: Apr. 15, 2016

(65) Prior Publication Data

US 2016/0222383 A1 Aug. 4, 2016

Related U.S. Application Data

(63) Continuation of application No. 14/570,293, filed on Dec. 15, 2014, now Pat. No. 9,314,434, which is a continuation of application No. 13/129,205, filed as application No. PCT/EP2009/008087 on Nov. 13, 2009, now Pat. No. 8,912,154.

(60) Provisional application No. 61/152,297, filed on Feb. 13, 2009.

(30) Foreign Application Priority Data

Nov. 13, 2008 (EP) .................................. 08425727

(51) Int. Cl.
| | | |
|---|---|---|
| *C12N 15/113* | (2010.01) | |
| *A61K 9/28* | (2006.01) | |
| *A61K 31/7125* | (2006.01) | |
| *A61K 9/00* | (2006.01) | |
| *A61K 31/7105* | (2006.01) | |

(52) U.S. Cl.
CPC ........ *C12N 15/1136* (2013.01); *A61K 9/0053* (2013.01); *A61K 9/2846* (2013.01); *A61K 31/7105* (2013.01); *A61K 31/7125* (2013.01); *C12N 15/113* (2013.01); *C12N 2310/11* (2013.01); *C12N 2310/315* (2013.01); *C12N 2320/32* (2013.01)

(58) Field of Classification Search
CPC .... A61K 48/00; A61K 31/713; C12N 15/113; C12N 15/111
See application file for complete search history.

(56) References Cited

U.S. PATENT DOCUMENTS

| | | | |
|---|---|---|---|
| 6,159,697 A | 12/2000 | Monia et al. | |
| 6,346,613 B1 | 2/2002 | O'Mahony et al. | |
| 7,465,444 B2 | 12/2008 | Watanabe | |
| 7,576,067 B2 | 8/2009 | Weinbach et al. | |
| 7,700,572 B2 | 4/2010 | Steinbrecher et al. | |
| 7,700,757 B2 | 4/2010 | Monteleone | |
| 7,807,818 B2 | 10/2010 | Monteleone | |
| 8,106,182 B2 | 1/2012 | Monteleone | |
| 8,648,186 B2 | 2/2014 | Monteleone | |
| 8,907,078 B2 | 12/2014 | Monteleone | |
| 8,912,154 B2 | 12/2014 | Baroni et al. | |
| 9,006,418 B2 | 4/2015 | Monteleone | |
| 9,096,854 B1 | 8/2015 | Monteleone | |
| 9,279,126 B2 | 3/2016 | Monteleone | |
| 9,314,434 B2 | 4/2016 | Baroni et al. | |
| 9,382,541 B2 | 7/2016 | Monteleone | |
| 9,499,819 B2 | 11/2016 | Baroni et al. | |
| 9,518,264 B2 | 12/2016 | Monteleone | |
| 9,605,264 B2 | 3/2017 | Monteleone | |
| 9,791,442 B2 | 10/2017 | Monteleone et al. | |
| 2001/0031278 A1 | 10/2001 | Oshlack et al. | |
| 2002/0102303 A1 | 8/2002 | Oshlack et al. | |
| 2005/0119203 A1 | 6/2005 | Steinbrecher et al. | |
| 2007/0042985 A1 | 2/2007 | Monteleone | |
| 2007/0167385 A1 | 7/2007 | Monteleone | |
| 2007/0243249 A1 | 10/2007 | Friesen et al. | |
| 2009/0156539 A1 | 6/2009 | Monteleone | |
| 2010/0317719 A1 | 12/2010 | Monteleone | |
| 2011/0207795 A1 | 8/2011 | Steinbrecher et al. | |
| 2011/0287093 A1* | 11/2011 | Schoenhard ........... | A61K 9/209 424/456 |
| 2012/0015033 A1 | 1/2012 | Baroni et al. | |
| 2012/0136043 A1 | 5/2012 | Monteleone | |
| 2013/0203839 A1* | 8/2013 | Monteleone ......... | C12N 15/113 514/44 A |
| 2014/0142163 A1 | 5/2014 | Monteleone | |
| 2014/0256788 A1 | 9/2014 | Monteleone | |
| 2014/0271860 A1 | 9/2014 | Monteleone et al. | |
| 2015/0125523 A1 | 5/2015 | Baroni et al. | |
| 2015/0148245 A1 | 5/2015 | Monteleone et al. | |
| 2015/0211011 A1 | 7/2015 | Monteleone | |

(Continued)

FOREIGN PATENT DOCUMENTS

| | | |
|---|---|---|
| EP | 0453001 A1 | 10/1991 |
| EP | 1080733 A1 | 3/2001 |

(Continued)

OTHER PUBLICATIONS

Nucleic Acids Research, 1997, 25, 18, pp. 3584-3589.*
Bijsterbosch et al. (1997) "In vivo fate of phosphorothioate antisense oligodeoxynucleotides: predominant uptake by scavenger receptors on endothelial liver cells," *Nucleic Acids Research* 24(16):3290-3296.
BPSI Holdings LLC "Preparation and Use Guidelines" (2011)(2 pages).
Celgene Corporation "Celgene Acquires Late-Stage Product for Crohn's Disease and Other Gastrointestinal Disorders" (2014)(2 pages).

(Continued)

*Primary Examiner* — Amy H Bowman
(74) *Attorney, Agent, or Firm* — Goodwin Procter LLP

(57) ABSTRACT

The present invention provides pharmaceutical formulations for oral administration of antisense oligonucleotides, such as antisense oligonucleotides against SMAD7. The pharmaceutical formulations can be used to treat Crohn's disease, ulcerative colitis and chronic inflammatory bowel disease.

19 Claims, 5 Drawing Sheets

(56) References Cited

U.S. PATENT DOCUMENTS

| | | |
|---|---|---|
| 2015/0218561 A1 | 8/2015 | Monteleone |
| 2015/0232854 A1 | 8/2015 | Baroni et al. |
| 2015/0315573 A1 | 11/2015 | Monteleone et al. |
| 2016/0177306 A1 | 6/2016 | Monteleone |
| 2016/0304876 A1 | 10/2016 | Monteleone |
| 2017/0107520 A1 | 4/2017 | Baroni et al. |
| 2017/0233736 A1 | 8/2017 | Monteleone et al. |
| 2017/0240893 A1 | 8/2017 | Monteleone |
| 2017/0253880 A1 | 9/2017 | Monteleone |

FOREIGN PATENT DOCUMENTS

| | | |
|---|---|---|
| WO | WO-1990/004386 A1 | 5/1990 |
| WO | WO-1991/016042 A1 | 10/1991 |
| WO | WO-1995/008339 A1 | 3/1995 |
| WO | WO-1997/045091 A2 | 12/1997 |
| WO | WO-1998/049348 A1 | 11/1998 |
| WO | WO-1999/016454 A1 | 4/1999 |
| WO | WO-1999/060012 A1 | 11/1999 |
| WO | WO-2003/017940 A2 | 3/2003 |
| WO | WO-2003/037368 A2 | 5/2003 |
| WO | WO-2004/087920 A1 | 10/2004 |
| WO | WO-2005/014011 A1 | 2/2005 |
| WO | WO-2005/092295 A1 | 10/2005 |
| WO | WO-2007/016350 A2 | 2/2007 |
| WO | WO-2007/047553 A2 | 4/2007 |
| WO | WO-2007/122374 A2 | 11/2007 |
| WO | WO-2008/122967 A2 | 10/2008 |
| WO | WO-2010/054826 A1 | 5/2010 |
| WO | WO-2013/037970 A1 | 3/2013 |
| WO | WO-2013/158868 A1 | 10/2013 |
| WO | WO-2014/140333 A1 | 9/2014 |
| WO | WO-2015/169966 A2 | 11/2015 |
| WO | WO-2016/016262 A1 | 2/2016 |
| WO | WO-2016/059239 A1 | 4/2016 |
| WO | WO-2016/059243 A2 | 4/2016 |
| WO | WO-2017/055611 A2 | 4/2017 |
| WO | WO-2017/144689 A1 | 8/2017 |

OTHER PUBLICATIONS

Colorcon "ACRYL-EZE® Aqueous Acrylic Enteric System" (2003)(2 pages).
Colorcon "ACRYL-EZE® Aqueous Acrylic Enteric System" (2006)(2 pages).
Colorcon "ACRYL-EZE® Aqueous Acrylic Enteric System" (2007)(2 pages).
Colorcon "Performance Characteristics of Acryl-Eze®, Aqueous Acrylic Enteric System" (2009)(5 pages).
Colorcon. Poster Reprint of Fegely K. et al. "Performance Characteristics of ACRYL-EZE™—a New, Fully-Formulated, Acrylic-Based, Enteric, Film-Coating System" (2001)(5 pages).
Coran, et al. (1983) "The Surgical Management of Terminal Ileal and Right Colon Crohn's Disease in Children," *Journal of Pediatric Surgery* 18(5):592-594.
European Patent Office Communication dated Oct. 2, 2014, issued in European Patent Application No. 09 756 431.4 (8 pages).
Evonik Röhm GmbH "Eudragite®: Acrylic Polymers for Solid Oral Dosage Forms" (2008) (11 pages).
Evonik Röhm GmbH "Guidelines for Formulation Development and Process Technology for Enteric Coatings" (2009)(3 pages).
Guo, et al. (2002) "Diffusion of a Freely Water-Soluble Drug in Aqueous Enteric-Coated Pellets," *AAPS PharmaSciTech* 3(2):1-8.
Hashmat, et al. (2008) "Development of Enteric Coated Flurbiprofen Tablets Using Opadry/acryl-eze System—A Technical Note," *AAPS PharmSciTech* 9(1):116-121.
International Search Report for PCT/EP2009/008087 dated May 6, 2010 (4 pages).
Monteleone et al. (2012) "Phase I Clinical Trial of Smad7 Knockdown Using Antisense Oligonucleotide in Patients With Active Crohn's Disease," *Molecular Therapy* 20(4):870-6.
Nozawa T. et al., (2003) "Enhanced intestinal absorption of drugs by activation of peptide transporter PEPT1 using proton-releasing polymer," *J Pharm Sci.* 92(11):2208-2216 (abstract only).
Official Action issued in Russian Patent Application No. 2011123876, dated Nov. 12, 2013, and English Translation (10 pages).
Patent Office of the Russian Federation Official Action, received Oct. 6, 2014, issued in Russian Patent Application No. 2011123876, English translation attached (9 pages).
Peppas NA et al., (2004) "Hydrogels for oral delivery of therapeutic proteins," *Expert Opin. Biol. Ther.* 4(6):1-7.
Pereira R.E.V. "pH-Sensitive Nanoparticles as Carriers for Oral Delivery of a Model Peptidomimetic Drug" Thesis, Universiti Teknologi Mara (2008)(pp. iii-xxiv only).
Pharma Polymers "Products and Services" p. 1-12 (2005).
Scherer et al., Nat. Biotechnol. 21(12):1457-1465 (2003).
Stein et al. (2011) "Therapeutic Oligonucleotides: The Road Not Taken," *Clin Cancer Res* 17(20):6369-6372.
te Velde et al. (2006) "Critical Appraisal of the Current Practice in Murine TNBS-induced Colitis," *Inflamm Bowel Dis* 12(10):995-999.
The Jackson Laboratory, "Sample TNBS-induced IBD Protocol," (2012) (3 pages).
Woodruff et al. (2005) "A potent and selective inhibitor of group IIa secretory phospholipase $A_2$ protects rats from TNBS-induced colitis," *International Immunopharmacology* 883-892.
Written Opinion of the International Searching Authority for PCT/EP2009/008087 dated May 6, 2010 (6 pages).
Zheng et al. (2000) "A chronic ulcerative colitis model in rats," *World Journal of Gastroenterology* 6(1):150-152.
Akhgari et al., (2005), "Statistical Optimization of Indomethacin Pellets Coated with pH-Dependent Methacrylic Polymers for Possible Colonic Drug Delivery," Int J Pharm, 305(1-2):22-30.
Deverre et al., (1997), 'A Competitive Enzyme Hybridization Assay for Plasma Determination of Phosphodiester and Phosphorothioate Antisense Oligonucleotides,' Nucleic Acids Res, 25(18):3584-9.
Wikberg et al., (1997), Review Article: Targeted Drug Delivery in Treatment of Intestinal Diseases, Aliment Pharmacol Ther, 11(Suppl 3):109-15.

* cited by examiner

SEQUENCE LISTING

```
<160> NUMBER OF SEQ ID NOS: 1

<210> SEQ ID NO 1
<211> LENGTH: 21
<212> TYPE: DNA
<213> ORGANISM: Artificial
<220> FEATURE:
```

```
<223> OTHER INFORMATION: oligonucleotide
<220> FEATURE:
<221> NAME/KEY: modified_base
<222> LOCATION: (3)..(3)
<223> OTHER INFORMATION: 5-methyl-2'-deoxycytidine
<220> FEATURE:
<221> NAME/KEY: modified_base
<222> LOCATION: (16)..(16)
<223> OTHER INFORMATION: 5-methyl-2'-deoxycytidine

<400> SEQUENCE: 1 gtcgccccttctccccgcag c                                                    21
```

ANTISENSE COMPOSITIONS AND METHODS OF MAKING AND USING SAME

RELATED APPLICATIONS

This application is a continuation of U.S. Ser. No. 14/570,293, filed Dec. 15, 2014, which is a continuation of U.S. Ser. No. 13/129,205, filed Sep. 30, 2011, which is a national stage filing under 35 U.S.C. § 371 of PCT/EP2009/008087, filed Nov. 13, 2009, which claims priority to applications EP08425727.8, filed Nov. 13, 2008, and U.S. Ser. No. 61/152,297, filed Feb. 13, 2009, each of which is hereby incorporated by reference in its entirety.

BACKGROUND

Ulcerative colitis and Crohn's disease are the major forms of chronic inflammatory bowel diseases (IBD) in humans. Intestinal bowel disease is an inappropriate immune response that occurs in genetically susceptible individuals as the result of a complex interaction among environmental factors, microbial factors and the intestinal immune system. It has been demonstrated that the excessive immune response to mucosal antigens inappropriately controlled by the normal counter-regulatory mechanisms leads to chronic intestinal inflammation.

Crohn's Disease is a chronic, relapsing inflammatory disease of the gastrointestinal tract, characterized by segmental transmural inflammation and granulomatous changes. Typical presentations include the discontinuous involvement of various portions of the gastrointestinal tract and the development of complications including strictures, abscesses or fistulas. Because its cause is unknown, medical management of Crohn's disease is largely empirical and is designed to reduce inflammation. Medical therapy includes corticosteroids, antibiotics, immunosuppressant drugs, and anti-TNFα agents. Due to the therapeutic failures and serious side effects of present therapies, alternatives are needed.

An important role in the pathogenesis of IBD is played by TGF-β1, a multifunctional cytokine capable of regulating the growth, differentiation, and function of immune and non-immune cells. A diminished ability to mount an efficient counter-regulatory TGF-β1 response to inflammatory stimuli is believed to be relevant in the pathogenesis of disease such as IBD. TGF-β1 acts as a potent negative regulator of mucosal inflammation and that the inhibition of its activity results in the development of colitis which shows immunomorphological similarities with Crohn's disease or ulcerative colitis.

In the inflamed intestine of patients with IBD there is marked over expression of Smad7 (a protein that serves as substrates for TGF-β1 receptors) and a reduction of Smad 3 phosphorylation, a crucial step in the TGF-β1 mediated signal transduction. Thus, in IBD, high levels of Smad7 may lead to a defective TGF-β1 signaling resulting in an over-expression of pro-inflammatory molecules genes and TGF-β1 does not exert its anti-inflammatory role.

Antisense oligodeoxynucleotide drugs are short chains of DNA nucleotides that inhibit protein translation by specifically binding to a small segment of messenger RNA (mRNA) responsible for driving the production of disease-causing proteins. The sequence of an antisense drug is designed to be complementary to its mRNA target such that, upon hybridization, the resulting double-stranded segment is recognized by the cell as abnormal and is destroyed, thereby preventing translation of the message into the protein product.

Antisense therapeutics, however, are typically administered parenterally which can lead to adverse reactions due to systemic effects. Such administration may also be unable to localize at the site of needed treatment. Therefore, there is a need for a topical-like application of antisense treatments for the treatment of IBD and related diseases using tablet based formulations.

SUMMARY

This disclosure is directed, at least in part, to pharmaceutical formulations for oral administration of antisense oligonucleotides, such as antisense oligonucleotides against SMAD7.

In an embodiment, a pharmaceutical tablet formulation for oral administration of an antisense oligonucleotide is provided that comprises an intra-granular phase, wherein the intra-granular phase includes an antisense oligonucleotide such as that represented by SEQ ID NO 1, or a pharmaceutically acceptable salt thereof (such as a sodium salt), and a pharmaceutically acceptable filler, and which may also include an extra-granular phase, that may include a pharmaceutically acceptable excipient such as a disintegrant. Contemplated oligonucleotides include those represented by SEQ ID NO 1, wherein at least one, or in certain embodiments, all, the internucleotide linkages are O,O-linked phosphorothioates.

The present disclosure provides for a tablet that includes a disclosed antisense oligonucleotide, and comprises an enteric coating. Such a tablet may, for example, include a filler, a disintegrant, and/or a lubricant. For example, provided herein is an oral dose form, such as a tablet, that comprises about 35 mg to about 500 mg of an antisense oligonucleotide, e.g. 40 mg of an oligonucleotide represented by SEQ ID NO 1 or a pharmaceutically acceptable salt thereof.

In an embodiment, provided herein is a tablet for oral use comprising: about 0.5% to about 10% by weight of an antisense oligonucleotide represented by SEQ ID NO 1 or a pharmaceutically acceptable salt thereof; about 30% to about 50% by weight mannitol; and about 10% to about 30% by weight microcrystalline cellulose.

For example, the disclosure provides a pharmaceutically acceptable tablet for oral use comprising an intra-granular phase and extra-granular phase, wherein for example, the intra-granular phase comprises about 5% to about 10%, by weight (for example about 8% by weight) of an antisense oligonucleotide represented by SEQ ID NO 1 or a pharmaceutically acceptable salt thereof, about 40% by weight mannitol, about 8% by weight microcrystalline cellulose, about 5% by weight hydropropylmethyl cellulose, and about 2% by weight sodium starch glycolate, and for example, the extra-granular phase comprises about 17% by weight microcrystalline cellulose, about 2% by weight sodium starch glycolate, and about 0.4% by weight magnesium stearate, where the tablet may further comprise an enteric coating.

Also provided herein are methods for treating Crohn's disease, ulcerative colitis, and chronic inflammatory bowel disease comprising administering to the patient in need thereof a tablet, oral dose or pharmaceutical formulation disclosed herein. For example, upon orally administering the pharmaceutical formulation, tablet or oral dosage form to a patient, the pharmaceutical formulation, tablet or oral dosage form may be substantially delivered to the terminal ileum and/or right colon of the patient.

DETAILED DESCRIPTION

Figure 1:
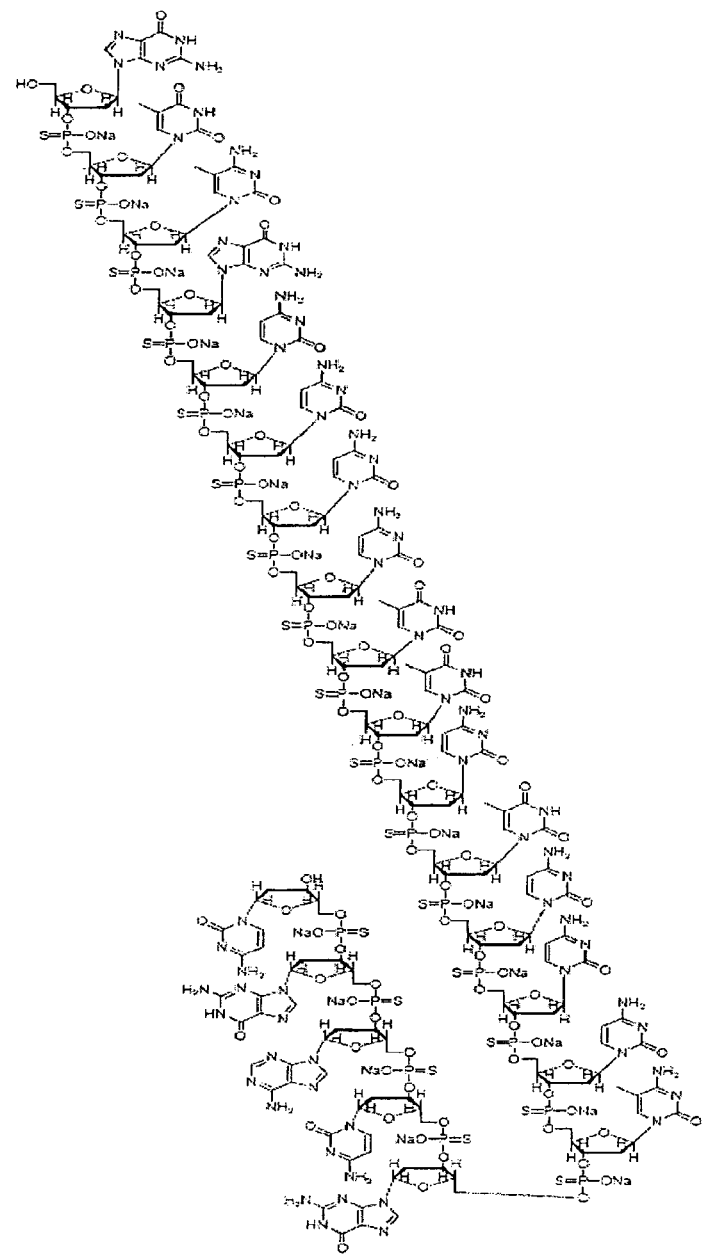
FIG. 1 depicts the molecular structure of an antisense compound, disclosed herein as AS1.

The present disclosure is generally directed to pharmaceutical compositions that include an antisense oligonucleotide, such as that depicted in FIG. 1. Contemplated compositions include oligonucleotides that act against Smad7, and may be administered orally. Disclosed compositions may, when administered orally, deliver an effective amount of an antisense oligonucleotide to the intestinal system of a patient, e.g. deliver an effective amount of an antisense oligonucleotide to the terminal ileum and/or right colon of a patient.

Contemplated antisense oligonucleotides include those comprising SEQ ID NO: 1 GTC*GCC CCT TCT CCC C*GC AGC, where C* represents 5-methyl-2'-deoxycytidine. In some embodiments, at least one of the internucleotide linkages of a contemplated antisense oligonucleotide is a O,O-linked phosphorothioate, for example, each of the 20 internucleotide linkages of SEQ ID NO:1 may be a O,O-linked phosphorothioate. In some embodiments, contemplated compositions disclosed herein may include a pharmaceutically acceptable salt, e.g. a sodium salt of the antisense oligonucleotide of SEQ ID NO:1, that optionally may include 1 to 20 O,O-linked phosphorothioate internucleotide linkages. Contemplated salts of oligonucleotides include those that are fully neutralized, e.g., each phosphorothioate linkage is associated with an ion such as $Na^+$. Oligonucleotides may include naturally occurring nucleobases, sugars, and covalent internucleoside (backbone) linkages as well as non-naturally occurring portions. An exemplary antisense oligonucleotide, referred herein as AS1, is shown in FIG. 1.

In some embodiments, contemplated herein are compositions suitable for oral delivery of an antisense oligonucleotide e.g., tablets, that include an enteric coating, e.g., a gastro-resistant coating, such that the compositions may deliver the antisense compound to e.g. the terminal ileum and right colon of a patient. For example, such administration may result in a topical effect, substantially topically applying the antisense compound directly to an affected portion of the intestine of a patient. Such administration, may, in some embodiments, substantially avoid unwanted systemic absorption of the antisense compound.

For example, a tablet for oral administration is provided that comprises granules (e.g., is at least partially formed from granules) that include a disclosed antisense compound, e.g., AS1, and pharmaceutically acceptable excipients. Such a tablet may be coated with an enteric coating. Contemplated tablets may include pharmaceutically acceptable excipients such as fillers, binders, disintegrants, and/or lubricants, as well as coloring agents, release agents, coating agents, sweetening, flavoring such as wintergreen, orange, xylitol, sorbitol, fructose, and maltodextrin, and perfuming agents, preservatives and/or antioxidants.

In some embodiments, contemplated pharmaceutical formulations include an intra-granular phase that includes a contemplated antisense compound, e.g. that depicted in SEQ ID NO. 1, or a pharmaceutically acceptable salt, e.g. AS1, and a pharmaceutically acceptable filler. For example, AS1 and a filler may be blended together, with optionally other excipients, and formed into granules. In some embodiments, the intragranular phase may be formed using wet granulation, e.g. a liquid (e.g., water) is added to the blended antisense compound and filler, and then combination is dried, milled and/or sieved to produce granules. One of skill in the art would understand that other processes may be used to achieve an intragranular phase.

In some embodiments, contemplated formulations include an extra-granular phase, which may include one or more pharmaceutically acceptable excipients, and which may be blended with the intragranular phase to form a disclosed formulation.

A disclosed formulation may include a intragranular phase that includes a filler. Exemplary fillers include, but are not limited to, cellulose, gelatin, calcium phosphate, lactose, sucrose, glucose, mannitol, sorbitol, microcrystalline cellulose, pectin, polyacrylates, dextrose, cellulose acetate, hydroxypropylmethyl cellulose, partially pregelatinized starch, calcium carbonate, and others including combinations thereof.

In some embodiments, a disclosed formulation may include a intragranular phase and/or a extragranular phase that includes a binder, which may generally function to hold the ingredients of the pharmaceutical formulation together. Exemplary binders include invention may be, but are not limited to, the following: starches, sugars, cellulose or modified cellulose such as hydroxypropyl cellulose, lactose, pregelatinized maize starch, polyvinyl pyrrolidone, hydroxypropyl cellulose, hydroxypropylmethyl cellulose, low substituted hydroxypropyl cellulose, sodium carboxymethyl cellulose, methyl cellulose, ethyl cellulose, sugar alcohols and others including combinations thereof.

Contemplated formulations, e.g., that include an intragranular phase and/or an extragranular phase, may include a disintegrant such as but are not limited to, starch, cellulose, crosslinked polyvinyl pyrrolidone, sodium starch glycolate, sodium carboxymethyl cellulose, alginates, corn starch, crosmellose sodium, crosslinked carboxymethyl cellulose, low substituted hydroxypropyl cellulose, acacia, and others including combinations thereof. For example, an intragranular phase and/or an extragranular phase may include a disintegrant.

In some embodiments, a contemplated formulation includes an intra-granular phase comprising a disclosed antisense compound and excipients chosen from: mannitol, microcrystalline cellulose, hydroxypropylmethyl cellulose, and sodium starch glycolate or combinations thereof, and an extra-granular phase comprising one or more of: microcrystalline cellulose, sodium starch glycolate, and magnesium stearate or mixtures thereof.

In some embodiments, a contemplated formulation may include a lubricant, e.g. an extra-granular phase may contain a lubricant. Lubricants include but are not limited to talc, silica, fats, stearin, magnesium stearate, calcium phosphate, silicone dioxide, calcium silicate, calcium phosphate, colloidal silicon dioxide, metallic stearates, hydrogenated vegetable oil, corn starch, sodium benzoate, polyethylene glycols, sodium acetate, calcium stearate, sodium lauryl sulfate, sodium chloride, magnesium lauryl sulfate, talc, and stearic acid.

In some embodiments, the pharmaceutical formulation comprises an enteric coating. Generally, enteric coatings create a barrier for the oral medication that controls the location at which the drug is absorbed along the digestive track. Enteric coatings may include a polymer that disintegrates a different rates according to pH. Enteric coatings may include for example, cellulose acetate phthalate, methyl acrylate-methacrylic acid copolymers, cellulose acetate succinate, hydroxylpropylmethyl cellulose phthalate, methyl methacrylate-methacrylic acid copolymers, ethylacrylate-methacrylic acid copolymers, methacrylic acid copolymer type C, polyvinyl acetate-phthalate, and cellulose acetate phthalate.

Exemplary enteric coatings include Opadry® AMB, Acryl-EZE®, Eudragit® grades. In some embodiments, an enteric coating may comprise about 5% to about 10%, about 5% to about 20%, 8 to about 15%, about 8% to about 18%, about 10% to about 12%, or about 12 to about 16%, of a contemplated tablet by weight. For example, enteric coatings may include an ethylacrylate-methacrylic acid copolymer.

For example, a tablet is provided that comprises or consists essentially of about 0.5% to about 70%, e.g. about 0.5% to about 10%, or about 1% to about 20%, by weight of an antisense oligonucleotide or a pharmaceutically acceptable salt thereof (e.g. AS1). Such a tablet may include for example, about 0.5% to about 60% by weight of mannitol, e.g. about 30% to about 50% by weight mannitol, e.g. about 40% by weight mannitol; and/or about 20% to about 40% by weight of microcrystalline cellulose, or about 10% to about 30% by weight of microcrystalline cellulose. For example, a disclosed tablet may comprise a intra granular phase that includes about 30% to about 60%, e.g. about 45% to about 65% by weight, or alternatively, about 5 to about 10% by weight AS1, about 30% to about 50%, or alternatively, about 5% to about 15% by weight mannitol, about 5% to about 15% microcrystalline cellulose, about 0% to about 4%, or about 1% to about 7% hydroxypropylmethylcellulose, and about 0% to about 4%, e.g. about 2% to about 4% sodium starch glycolate by weight.

Exemplary formulations include dosage forms that include or consist essentially of about 35 mg to about 500 mg of AS1, for example, tablets that include about 35 mg, 40 mg, 50 mg, 60 mg, 70 mg, 80 mg, 90 mg, 100 mg, 150 mg, 200 mg, or 250 mg of AS1 are contemplated herein.

In an exemplary embodiment, a pharmaceutically acceptable tablet for oral administration is provided that includes a intra-granular phase that may comprise about 50% by weight AS1 (or salt thereof), about 11.5% by weight mannitol, about 10% by weight microcrystalline cellulose, about 3% by weight hydropropylmethylcellulose, and about 2.5% by weight sodium starch glycolate; and an extra-granular phase that may comprise about 20% by weight microcrystalline cellulose, about 2.5% by weight sodium starch glycolate, and about 0.5% by weight magnesium stearate. The tablet may also include an enteric coating.

In another exemplary embodiment, a pharmaceutically acceptable tablet for oral administration is provided that includes or consists essentially of: a intra-granular phase that may comprise or consist essentially of about 5% to about 10%, e.g., about 8% by weight AS1 (e.g. wherein the internucleotide linkages are each O,O-linked phophorothioates, and/or salt thereof, e.g. a sodium salt), about 40% by weight mannitol, about 8% by weight microcrystalline cellulose, about 5% by weight hydropropylmethylcellulose, and about 2.% by weight sodium starch glycolate; and an extra-granular phase that may comprise about 17% by weight microcrystalline cellulose, about 2% by weight sodium starch glycolate, and about 0.4% by weight magnesium stearate.

Disclosed tablets may also include an enteric coating, e.g., a disclosed tablet may include about 13%, about 15%, 16%, 17% by weight of an enteric coating, e.g. AcyrlEZE®.

The rate at which point the coating dissolves and the active ingredient is released is its dissolution rate. In an embodiment, a contemplated tablet may have a dissolution profile, e.g. when tested in a USP/EP Type 2 apparatus (paddle) at 100 rpm and 37° C. in a phosphate buffer with a pH of 7.2, of about 50% to about 100% of the oligonucleotide releasing after about 120 minutes to about 240 minutes, for example after 180 minutes. In another embodiment, a contemplated tablet may have a dissolution profile, e.g. when tested in a USP/EP Type 2 apparatus (paddle) at 100 rpm and 37° C. in diluted HCl with a pH of 1.0, where substantially none of the oligonucleotide is released after 120 minutes. A contemplated tablet, in another embodiment, may have a dissolution profile, e.g. when tested in USP/EP Type 2 apparatus (paddle) at 100 rpm and 37° C. in a phosphate buffer with a pH of 6.6, of about 10% to about 30%, or not more than about 50%, of the oligonucleotide releasing after 30 minutes.

Disclosed formulations, e.g. tablets, in some embodiments, when orally administered to the patient may result in minimal plasma concentration of the oligonucleotide in the patient. In another embodiment, disclosed formulations, when orally administered to a patient, topically deliver to the terminal ileum and/or right colon of a patient, e.g. to an affected or diseased intestinal site of a patient.

Also provided herein are methods of treating Crohn's disease, ulcerative colitis, and/or chronic inflammatory bowel disease in a patient in need thereof administering a disclosed formulation.

EXAMPLES

The examples that follow are intended in no way to limit the scope of this invention but are provided to illustrate the methods of the present invention. Many other embodiments of this invention will be apparent to one skilled in the art.

Example 1—Tablets

Figure 2:
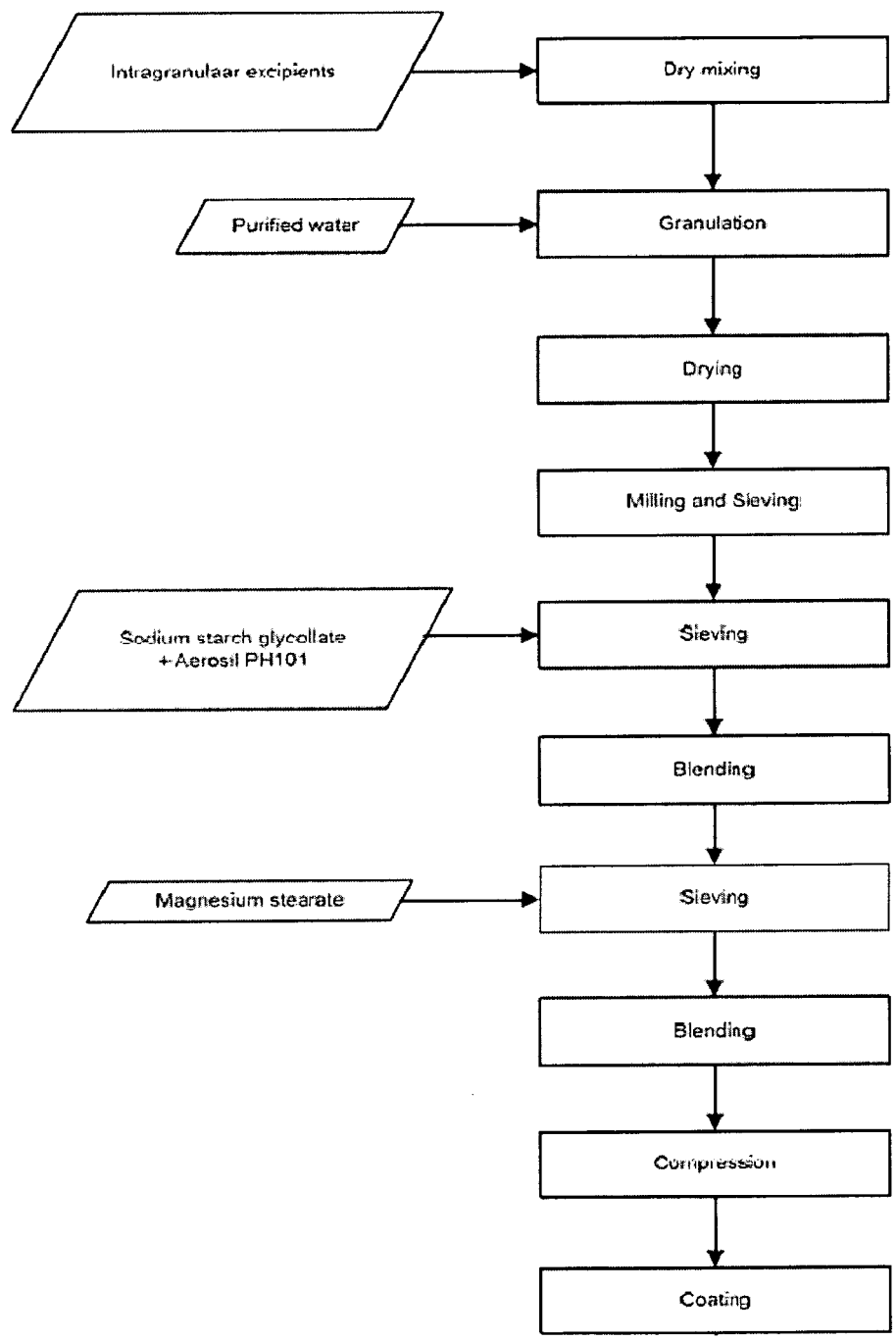
FIG. 2 is a schematic of the manufacturing process for AS1.

Wet granules were prepared by dispensing each intra-granular component into an appropriate container. All of the intra-granular materials were screened through a 710 µm sieve and blended in a food processor bowl for around 5 minutes. Water granulating fluid was added slowly using a syringe. The wet mass was passed through 2.00 mm hand screen and dried in an oven at 40° C. for up to 90 minutes. After drying, the granules were screened through 1.00 mm hand screen. A mortar and pestle was employed to reduce the size of the coarse granules. The granules were blended with the extra-granular excipients except magnesium stearate using a Turbula blender for 10 minutes at 42 rpm. Magnesium stearate was added to the blend and further mixed for 2 minutes at 42 rpm. Formulations were compressed on a Manesty F3 single punch compression machine. An overall manufacturing process flow diagram for the AS1 tablets may be seen in FIG. 2.

The mannitol based 250 mg dose strength formulation made at a 50 g batch size had a moisture content of the dry mix of 5.21% and a moisture content of the dried granules of 6.42%. The mannitol based 250 mg dose strength formulation had 5.0 g of water added, a granulation time of 4 minutes, and a drying time of 60 minutes.

The mannitol based 35 mg dose strength made at a 100 g batch size had a moisture content of 2.35% for the dried granules, 28 g of water was added, 6 minutes of granulation time, and had a drying time of 65 minutes.

The compression IPC results for the mannitol based 250 mg dose strength formulations are as follows: average weight of 453.0 mg, a hardness of 18.0 Kp, a thickness of 3.82 mm, a friability of 0.23%, and a disintegration of 17 minutes.

Table 1A includes tablet compositions for three dose strengths: 3.5 mg, 35 mg, and 250 mg. Tablet weight was 500 mg for all formulations.

TABLE 1A

| Materials | 3.5 mg (% w/w) | 35 mg (% w/w) | 250 mg (% w/w) |
|---|---|---|---|
| Intra-granular | | | |
| AS1 active | 0.7 | 7.0 | 50.0 |
| Mannitol | 57.8 | 51.5 | 11.5 |
| Microcrystalline cellulose | 10.0 | 10.0 | 10.0 |
| Hydroxypropylmethyl cellulose | 6.0 | 6.0 | 3.0 |
| Sodium starch glycolate | 2.5 | 2.5 | 2.5 |
| Extra-granular | | | |
| Microcrystalline cellulose | 20.0 | 20.0 | 20.0 |
| Sodium starch glycolate | 2.5 | 2.5 | 2.5 |
| Magnesium stearate | 0.5 | 0.5 | 0.5 |
| Total | 100.0 | 100.0 | 100.0 |

TABLE 1B indicates composition of core batches of these three dose strengths:

| Materials % w/w | Batch 1 | Batch 2 | Batch 3 |
|---|---|---|---|
| Batch Size (units) | 630 | 862 | 376 |
| Intra-granular | | | |
| AS1 active | 7.0 | 50.0 | 62.5 (corrected to potency, equiv. to 40% w/w pure AS1) |
| Mannitol | 51.5 | 11.5 | 1.7 |
| Microcrystalline cellulose | 10.0 | 10.0 | 7.3 |
| Hydroxypropylmethyl cellulose | 6.0 | 6.0 | 3.0 |
| Sodium starch glycolate | 2.5 | 2.5 | 2.5 |
| Extra-granular | | | |
| Microcrystalline cellulose | 20.0 | 20.0 | 20.0 |
| Sodium starch glycolate | 2.5 | 2.5 | 2.5 |
| Magnesium stearate | 0.5 | 0.5 | 0.5 |
| Total | 100.0 | 100.0 | 100.0 |

Example 2—Powder Characterization

Figure 3:
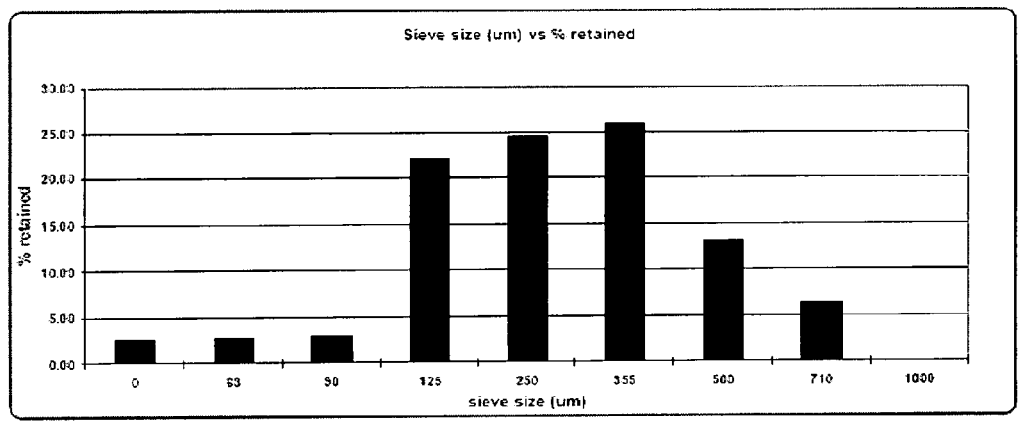
FIG. 3 is a bar graph depicting the particle size distribution for the 3.5 mg dose strength of AS1.
Figure 4:
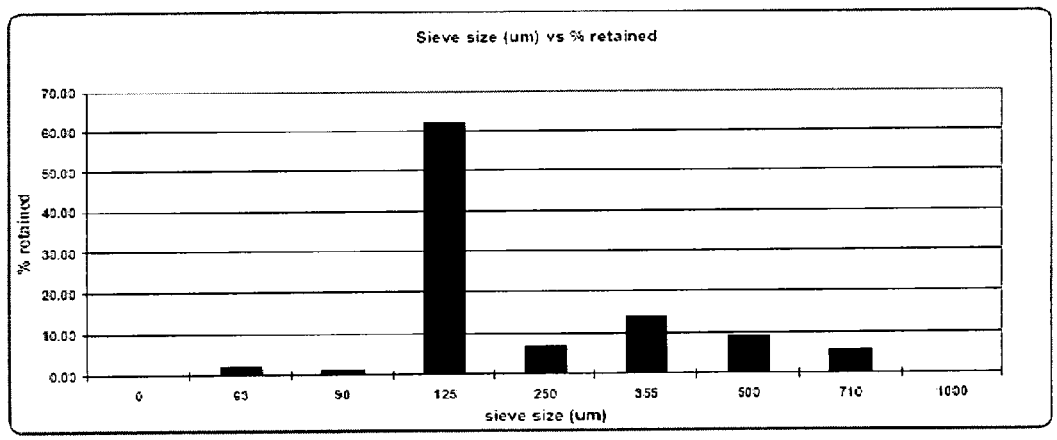
FIG. 4 is a bar graph depicting the particle size distribution for the 35 mg dose strength of AS1.
Figure 5:
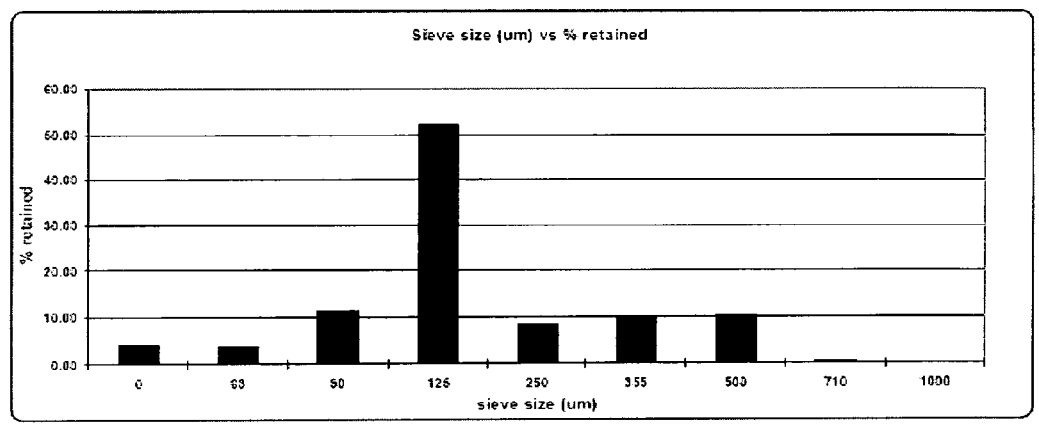
FIG. 5 is a bar graph depicting the particle size distribution for the 250 mg dose strength of AS1.

Formulations were assessed for particle size distribution, density, Carr's index and angle of repose. Particle size analysis indicated that particles are bigger in size (335 μm) for 3.5 mg dose strength formulation, whereas 35 mg and 250 mg dose strength formulations exhibited usual particle size distribution. FIG. 3 depicts the particle size distribution for the 3.5 mg dose strength with the composition indicated in Table 1. FIG. 4 depicts the particle size distribution of the 35 mg dose strength with the composition indicated in Table 1. Finally, FIG. 5 depicts the particle size distribution for the 250 mg dose strength with the composition as indicated in Table 1. Table 2 presents the powder characterization results for the three dose strengths.

TABLE 2

| Properties | 3.5 mg | 35 mg | 250 mg |
|---|---|---|---|
| Angle of repose (°) | 39.5 | 36.5 | 35.0 |
| Poured bulk density (g · cm$^{-3}$) | .069 | 0.62 | 0.63 |
| Tapped bulk density (g · cm$^{-3}$) | 0.75 | 0.72 | 0.72 |
| Carr's compressibility index (%) | 8.0 | 13.9 | 12.5 |
| Median particle size (μm) | 335 | 219 | 199 |

Example 3—Enteric Coating

A 20% coating solution was prepared for Acryl-EZE® coatings. The required quantities of water and Acryl-EZE® were dispensed in appropriate containers. While mixing, Acryl-EZE® was added slowly to the vortex. The dispersion was stirred for 45 mins and passed through a 500 μm sieve. The spraying was continued until a weight gain of 10% or 16% was obtained.

Example 4—40 mg Tablets

A batch formula for 40 mg tables of AS1 is depicted below:

| Materials | % w/w | g |
|---|---|---|
| Intra-granular | | |
| AS1 active | 8.02% (*) | 188.66 |
| Mannitol | 40.47% (*) | 952 |
| Microcrystalline cellulose | 8.29% | 195 |
| Hydroxypropylmethylcellulose | 4.97% | 117 |
| Sodium starch glycolate | 2.07% | 48.75 |
| Extra-granular | | |
| Microcrystalline cellulose | 16.58% | 390 |
| Sodium starch glycolate | 2.07% | 48.8 |
| Magnesium stearate | 0.42% | 9.8 |
| Opadry ® AMB | 3.32% | 78 |
| AcrylEZE ® | 13.79% | 324.5 |
| Total | 100.0 | 100.0 |

(*) Correction to potency is applied to account for API moisture and purity; mannitol is adjusted accordingly.

Example 5—200 mg Tablet Formulation

An AS1 tablet at 200 mg dose strength was manufactured generally following the procedure in Example 1, as shown in Table 4. The tablet weight for all the formulations was 500 mg.

TABLE 4

Composition of the formulation at 200 mg dose strength

| Materials | 200 mg Dose Strength (% w/w) |
|---|---|
| Intra-granular | |
| AS1 active | 62.5 |
| Mannitol | 1.7 |
| Microcrystalline cellulose | 7.3 |
| Hydroxypropylmethyl cellulose | 3.0 |
| Sodium starch glycolate | 2.5 |
| Extra-granular | |
| Microcrystalline cellulose | 20.0 |
| Sodium starch glycolate | 2.5 |
| Magnesium stearate | 0.5 |

Example 6—HPLC Dissolution Method

This analytical test procedure describes a dissolution analysis of AS1 enteric coated tablets by HPLC. Dissolution is preformed following the Ph. Eur. Procedure for delayed release solid dosage forms, using Method A. Apparatus used was Ph. Eur./USP apparatus 2 (paddle).

The dissolution conditions for the HPLC are as follows: the media consists of pH 1.0 HCl (120 mins), pH 6.6 (30 mins), pH 7.2 (60 mins); a temperature of 37° C.; a rate of 100 rpm; sample to recycle 7.5 ml, sample size 0.8 ml; sample times 120 min in pH 1.0 HCl, 15, 30 min pH 6.6, 15, 30, 45, 60 min pH 7.2; and a 45 μm Disteck in-line filter.

Media was adjusted in each vessel during the dissolution at each state as follows: the initial volume 750 ml pH 1.0 HCl; at 120 mins, 200 ml of 0.2 M $Na_3PO_4$ and 30 ml 1.0 M pH 6.7 $Na_2HPO_4$ was added followed by the adjustment of the pH to pH 6.60±0.05 with 2.0 M NaOH; at 150 mins, followed by the adjustment of the pH to 7.20±0.05 with 2.0 M NaOH.

The chromatographic conditions are as follows: a Dionex HPLC analytical column, DNAPac-100, 4×250 mm; a flow rate of 2.0 ml/min; a column temperature of 80° C.; detection of UV at 260 nm; an injection volume of 100 μl; a needle wash of water; a mobile phase of A) 10% v/v acetonitrile in 100 mM Tris (pH 8.0) and B) 10% v/v acetonitrile in 100 mM Tris and 2M LiCl (pH 8.0); an HPLC run time of 15 mins; and an elution period of AS1 at approximately 6 minutes. The gradient is presented in Table 6.

TABLE 6

| Time (min) | Flow (ml/min) | % A | % B | Curve |
|---|---|---|---|---|
| Initial | 2.0 | 70 | 30 | — |
| 6.0 | 2.0 | 0 | 100 | 6 |
| 10.0 | 2.0 | 0 | 100 | 6 |
| 11.0 | 2.0 | 70 | 30 | 6 |

Preparation of 35 mg Tablets working standard solutions: 12.5 mg of AS1 reference standard was placed into 50 ml volumetric flask and dissolved with water to make 50 ml solution. 7 ml of the solution was diluted with water to make a 50 ml solution yielding a final concentration of AS1 of 0.035 mg/ml.

Preparation of 250 mg tablets working standard solutions: 12.5 mg of AS1 is placed in a 50 ml volumetric flask and dissolved with water to 50 ml volume yielding a final concentration of AS1 of 0.25 mg/ml.

Figure 6:
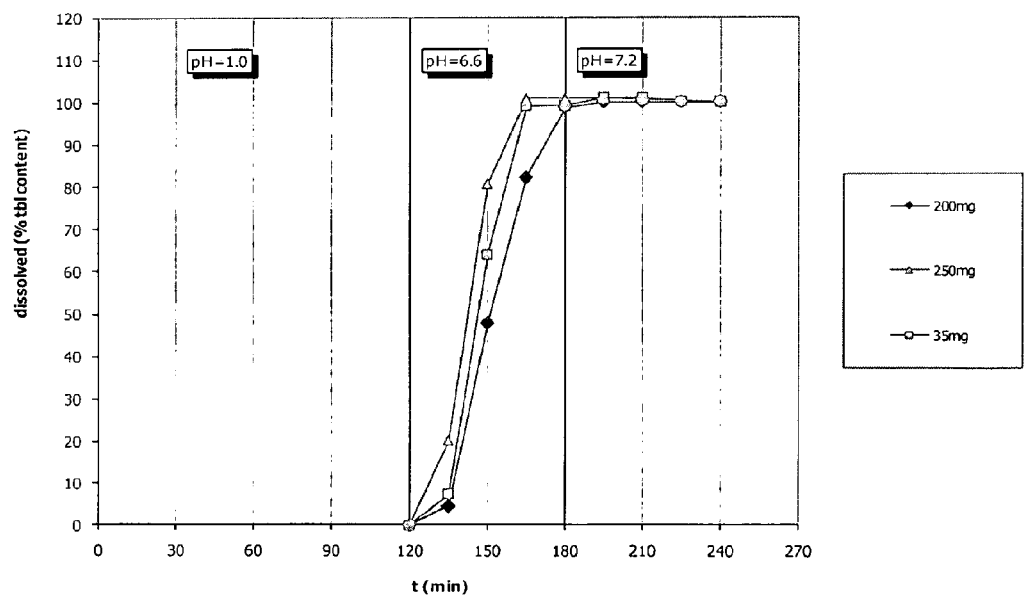
FIG. 6 is a line graph presenting the dissolution profiles (as a percentage of tablet dissolved) for three tablets with different dose strengths of AS1 in three different media (pH 1.0, pH 6.6, and pH 7.2).

Table 5 presents the dissolution results for the 35 mg, 250 mg, and 200 mg batches, with a 12% weight gain Acryl-EZE® coating. FIG. 6 is a graph of the dissolution profiles for tablets with three dose sizes of AS1 formulations in three different mediums.

TABLE 5

| | % AS1 Dissolved Time (min): | | | |
|---|---|---|---|---|
| | 120 | 150 | 180 | 210 |
| | Media: | | | |
| | pH 1.0 | pH 6.6 | pH 7.2 | pH 7.2 |
| 35 mg (batch 1) | 0.0 | 51.0 | 80.0 | 81.0 |
| 250 mg (batch 2) | 0.0 | 62.0 | 78.0 | 78 |
| 200 mg (batch 3) | 0.0 | 46.0 | 97.0 | 98.0 |

Figure 7:
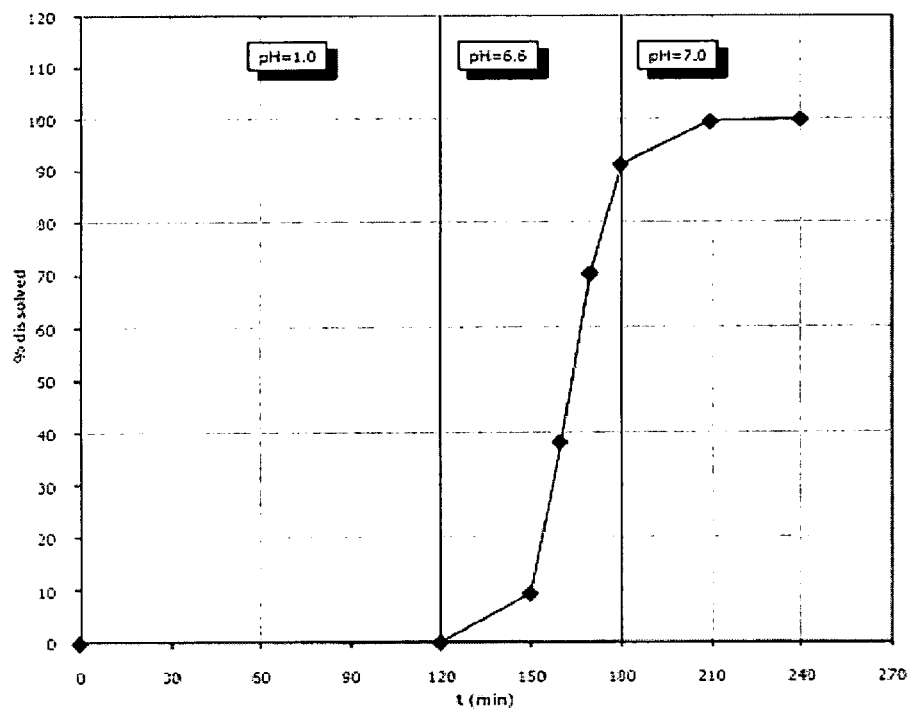
FIG. 7 depicts the dissolution profile of a batch described herein.

Tablets with 16% coating of Acryl-EZE® are made using tablets as described above in Batch 1, and the final coating is conducted until the weight gain of the tablets into the coating pan is 16% of the starting value. FIG. 7 depicts the dissolution profile.

Example 7—In Vivo Oral Dosing of AS1

The objectives of the study were to identify the potential effects of AS1 on cardiovascular, respiratory, and central nervous systems of conscious, unrestrained, cynomolgus monkeys when administered a single dose by oral administration or intravenous administration. The intravenous administration in this study was included to investigate potential effects associated with systemic exposure. The intravenous dose formulation was administered as bulk powder and for oral administration as enteric coated tablets contained within gelatin capsules. Four experimentally non-naïve cynomolgus male monkeys, 3.6 to 3.8 years of age, and weighing 3.4 to 3.9 kg were assigned to a single group.

TABLE 7

| No. of Animals (male) | Dosing Days | Nominal Dose Level (mg/kg) | Dose Volume (ml/kg) | Dose Concentration (mg/ml) | Dose Route |
|---|---|---|---|---|---|
| 4 | 1 | 0 | N/A | N/A | Oral |
| 4 | ~13.4-14.9 | N/A | N/A | N/A | Oral |
| 7 | ~87.1-97.1 | N/A | N/A | N/A | Oral |
| 12 | 0 | 1 | 0 | | IV |
| 14 | 3 | | 3 | | IV |
| 19 | 10 | | 10 | | IV |

All dose levels represent the quantity of AS1, corrected for purity. The control oral doses was two capsules containing placebo tablets. Approximate dose level, achieved by administration of two capsules, each containing a tablet with 26.1 mg AS1 per tablet (corrected for purity), and based on body weights that ranged from 3.5 to 3.9 kg on Day 4. Approximate dose level, achieved by administration of two capsules, each containing tablet with 169.9 mg AS1 per tablet (corrected for purity), and based on body weights that ranged from 3.5 to 3.9 kg on Day 4.

Blood samples for toxicokinetic analysis were collected prestudy and 1 and 6 hours post dose for oral doses and 5 minutes, 1 and 6 hours post dose for intravenous doses. The samples were processed to plasma under refrigerated conditions and the plasma was stored at −70° C. until analyzed. The samples were analyzed using the AS1 specific hybridization assay.

On Day 1, all animals received the oral control article dose, followed by doses of AS1 on Days 4 and 7 via oral gavage. For the oral doses, the placebo and AS1 containing tablets were contained within appropriate size gelation capsules to facilitate administration via the oral route. On Day 12, all animals received the intravenous control dose (phosphate-buffered saline) by slow push injection, followed by intravenous doses of AS1 on Days 14 and 19.

Cardiovascular data and body temperature data were recorded via telemetry at frequent intervals prior to and for 24 hours following each dose administration. Respiratory function was assessed by measurement of blood gas parameters in arterial samples collected prior to dosing and 1, 6, and 24 hours following each dose, as well as by determining respiration rate (visually) at those same time points. Neurologic function was assessed by performing a comprehensive neurologic examination of all animals prior to the study within approximately 24 hours after the end of the telemetry recording period following the last oral dose of test article and again within approximately 24 hours after the end of the telemetry recording period following the last intravenous dose. Animals were also observed for clinical signs (mortality/morbidity, cage side observations, food consumption, and body weight).

Despite a very low LLOQ for the assay (0.5 ng/ml), AS1 was not detected in any plasma samples following oral doses up to nearly 100 mg/kg. In contrast, mean maximum plasma concentrations following IV injections were 28,309 and 180,352 ng/ml for the 3 and 10 mg/kg doses, respectively. Clearance of AS1 from the plasma following IC dosing exhibited kinetics similar to what has been reported for structurally related oligonucleotides (i.e., an approximate 0.5-hour half-life).

Example 8—28 Day In-Vivo Study of AS1 Administered Orally

The purpose of this study was to evaluate the potential toxicity and toxicokinetics of AS1 when administered once daily orally to mice for 28 days followed by a 28 day recovery period. The AS1 formulation was prepared as a formulation containing a gastro-protective coating in the form of small coated beads AS1 was layered onto inert beads which were then coated with Eudragit® S 100 to mimic the oral formulations suitable for human use. Three groups administered different dose levels were used (30 mg/kg/day (low); 100 mg/kg/day; 300 mg/kg/day).

There were no gender-related differences in plasma or tissue levels. Despite a very low LLOQ for the assay, AS1 was detected in only two plasma samples from very low dose (30 mg/kg/day) animals collected on Day 1 and not in any samples collected on Day 28. At the higher dose levels of 100 and 300 mg/kg/day, AS1 was quantifiable in most plasma samples, and the levels were generally dose related. However, even at the highest dose level, the plasma levels did not exceed 21 ng/ml in any animal (in samples collected at various times between 0.5 and 24 hours post-dose). AS1 concentrations were very high in gastrointestinal (GI) tissues, with mean maximal concentrations at the highest dose level (following the first dose) of approximately 536, 857, 825, 538, 137 and 127 µg/gram of tissue for large intestine, small intestine, forestomach, glandular stomach, esophagus and rectum, respectively.

Extensive clearance from the GI tract tissues was evident by 24 hours after the first dose. There was no apparent accumulation of AS1 with daily dosing.

Maximal mean concentrations in the two major organs of systemic uptake, kidney and liver, following the first dose of 300 mg/kg were only 4.0 and 2.3 µg/gram, which is over 100 times lower than the range of concentrations measured in GI tissues.

Following the lowest dose of 30 mg/kg, the highest kidney and liver mean concentrations were only 0.4 and 0.3 µg/gram. There was no evidence for accumulation of AS1 in internal organs over the 28 day dosing period.

Systemic exposure to AS1 in mice was very low following oral administration of high doses (up to 300 mg/kg/day) of AS1, delivered in gastro-protected formulation and there was no accumulation in GI tissues or internal tissues when administered daily for 28 consecutive days.

Example 9—Therapeutic Effect of AS1 on Colitis

To examine the therapeutic effect of AS1 on the course of the intestinal inflammation in the TNBS-induced colitis model, mice were treated with a single dose of AS1 or Smad7 sense oligonucleotide one day following intra-rectal administration of TNBS. Single doses of 125 or 250 µg/mouse ameliorated weight loss and markedly reduced the severity histological manifestations of colitis.

AS1 (given as a single 125 µg dose one day after TNBS-colitis induction) significantly reduced the colonic production of the monomeric p40 subunit, a component of IL-12 and IL-23 cytokines, demonstrating inhibition of colonic production of these pro-inflammatory cytokines.

All publications and patents mentioned herein, including those items listed below, are hereby incorporated by reference in their entirety as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

The invention claimed is:

1. A method for confirming topical delivery of an oligonucleotide of SEQ ID NO: 1, or a pharmaceutically acceptable salt thereof, substantially to the terminal ileum and/or right colon of a human following administration to the human of an oral dosage form comprising the oligonucleotide of SEQ ID NO: 1 or the pharmaceutically acceptable salt thereof, and an enteric coating, wherein the method comprises measuring plasma concentration of the oligonucleotide, or a pharmaceutically acceptable salt thereof, in the human; wherein minimal or absent plasma concentration of the oligonucleotide, or a pharmaceutically acceptable salt thereof, confirms topical delivery of the oligonucleotide, or a pharmaceutically acceptable salt thereof, substantially to the terminal ileum and/or right colon of the human.

2. The method of claim 1, wherein the plasma concentration is measured using a hybridization assay specific for the oligonucleotide.

3. The method of claim 1, wherein all internucleoside linkages in the oligonucleotide or the pharmaceutically acceptable salt thereof are O,O-linked phosphorothioates.

4. The method of claim 1, wherein the enteric coating comprises cellulose acetate phthalate, methyl acrylate-methacrylic acid copolymer, cellulose acetate succinate, hydroxypropylmethyl cellulose phthalate, methyl methacrylate-methacrylic acid copolymer, ethylacrylate-methacrylic acid copolymer, methacrylic acid copolymer type C, polyvinyl acetate phthalate or cellulose acetate phthalate.

5. The method of claim 4, wherein the enteric coating comprises ethylacrylate-methacrylic acid copolymer.

6. The method of claim 1, wherein the oral dosage form comprises about 5% to about 20% by weight of the enteric coating.

7. The method of claim 1, wherein the oral dosage form comprises about 8% to about 18% by weight of the enteric coating.

8. The method of claim 1, wherein the oral dosage form comprises about 8% to about 15% by weight of the enteric coating.

9. The method of claim 1, wherein the oral dosage form comprises about 10% to about 12% by weight of the enteric coating.

10. The method of claim 1, wherein the oral dosage form comprises about 12% to about 16% by weight of the enteric coating.

11. The method of claim 1, wherein the oral dosage form comprises about 10%, about 12%, about 13%, about 15%, about 16%, or about 17% by weight of the enteric coating.

12. The method of claim 1, wherein the oral dosage form comprises about 10% by weight of the enteric coating.

13. The method of claim 1, wherein the oral dosage form comprises about 12% by weight of the enteric coating.

14. The method of claim 1, wherein the human is a chronic inflammatory bowel disease patient.

15. The method of claim 1, wherein the human is a Crohn's disease patient.

16. The method of claim 1, wherein the human is an ulcerative colitis patient.

17. The method of claim 1, wherein the oral dosage form is a tablet.

18. The method of claim 1, wherein the oral dosage form comprises about 35 mg to about 500 mg of the oligonucleotide or the pharmaceutically acceptable salt thereof.

19. A method for confirming topical delivery of a SMAD7 antisense oligonucleotide, or a pharmaceutically acceptable salt thereof, substantially to the terminal ileum and/or right colon of a human following administration to the human of an oral dosage form comprising the SMAD7 antisense oligonucleotide, or the pharmaceutically acceptable salt thereof, and an enteric coating, wherein the method comprises measuring plasma concentration of the SMAD7 antisense oligonucleotide, or the pharmaceutically acceptable salt thereof, in the human; wherein minimal or absent plasma concentration of the SMAD7 antisense oligonucleotide, or the pharmaceutically acceptable salt thereof, confirms topical delivery of the antisense oligonucleotide, or the pharmaceutically acceptable salt thereof, substantially to the terminal ileum and/or right colon of the human.

* * * * *